US00PP32879P2

(12) United States Plant Patent
Gallagher

(10) Patent No.: US PP32,879 P2
(45) Date of Patent: Mar. 9, 2021

(54) WILLOW OAK TREE NAMED 'TGO-GAL'

(50) Latin Name: *Quercus phellos*
Varietal Denomination: TGO-GAL

(71) Applicant: Terrance Daniel Gallagher, McMinnville, TN (US)

(72) Inventor: Terrance Daniel Gallagher, McMinnville, TN (US)

( * ) Notice: Subject to any disclaimer, the term of this patent is extended or adjusted under 35 U.S.C. 154(b) by 0 days.

(21) Appl. No.: 16/602,920

(22) Filed: Dec. 23, 2019

(51) Int. Cl.
*A01H 5/04* (2018.01)
*A01H 6/00* (2018.01)

(52) U.S. Cl.
USPC ..... Plt./225
CPC ..... *A01H 6/00* (2018.05)

(58) Field of Classification Search
USPC ..... Plt./225
CPC ..... A01H 6/00
See application file for complete search history.

*Primary Examiner* — Anne Marie Grunberg
(74) *Attorney, Agent, or Firm* — Samuel R. McCoy, Jr.

(57) ABSTRACT

A new and distinct *Quercus phellos* tree named 'TGO-GAL' which is characterized by a dominant central leader with an upright ascending and freely branching growth habit, an oval to pyramidal tree crown profile, red juvenile foliage in spring and autumn, and mature foliage which fades to yellow prior to leaf abscission in autumn. The claimed plant propagates successfully by softwood stem cuttings and has proven to be uniform and stable in the resulting generations.

3 Drawing Sheets

Latin name of the genus and species: The Latin name of the genus and species of the novel variety disclosed herein is *Quercus phellos.*

Variety denomination:

The inventive variety of *Quercus phellos* disclosed herein has been given the variety denomination 'TGO-GAL'.

BACKGROUND OF THE INVENTION

Parentage: The claimed plant is the product of a chance discovery which was found at a commercial tree nursery in Warren County, Tenn. In January of 2007, the claimed plant was discovered growing amongst a cultivated population of openly-pollinated, unnamed *Quereus phellos* seedling trees (not patented) growing in a production field. Said seedling exhibited a strong central leader with a narrower and more upright growth habit when compared to other *Quercus phellos* seedlings. The tree was isolated and grown to a mature size to confirm the distinctness and stability of the characteristics initially observed. Upon further evaluation and confirmation of the desirable traits, the claimed tree was finally selected for commercialization in 2015 and given the variety denomination, 'TGO-GAL'.

Asexual Reproduction: In 2009, 'TGO-GAL' was first asexually reproduced in Warren County, Tenn. by way of softwood stem cuttings and has since further been asexually propagated by way of grafting. The claimed tree was found to asexually reproduce in uniform and stable manner and 3 successive cycles of vegetative propagation have proven to be true to type.

SUMMARY OF THE INVENTION

The following characteristics have been repeatedly observed and represent the distinguishing characteristics of the new *Quercus phellos* tree, 'TGO-GAL'. These traits, in combination, distinguish 'TGO-GAL' as a new and distinct cultivar.

1. 'TGO-GAL' exhibits an upright ascending, freely branching growth habit and an oval to pyramidal tree crown profile; and
2. 'TGO-GAL' exhibits a near-vertical, dominant central leader; and
3. 'TGO-GAL' exhibits red juvenile foliage in spring and autumn; and
4. 'TGO-GAL' exhibits mature foliage which fades to yellow prior to leaf abscission in autumn.

BOTANICAL DESCRIPTION OF THE PLANT

Figure 1:
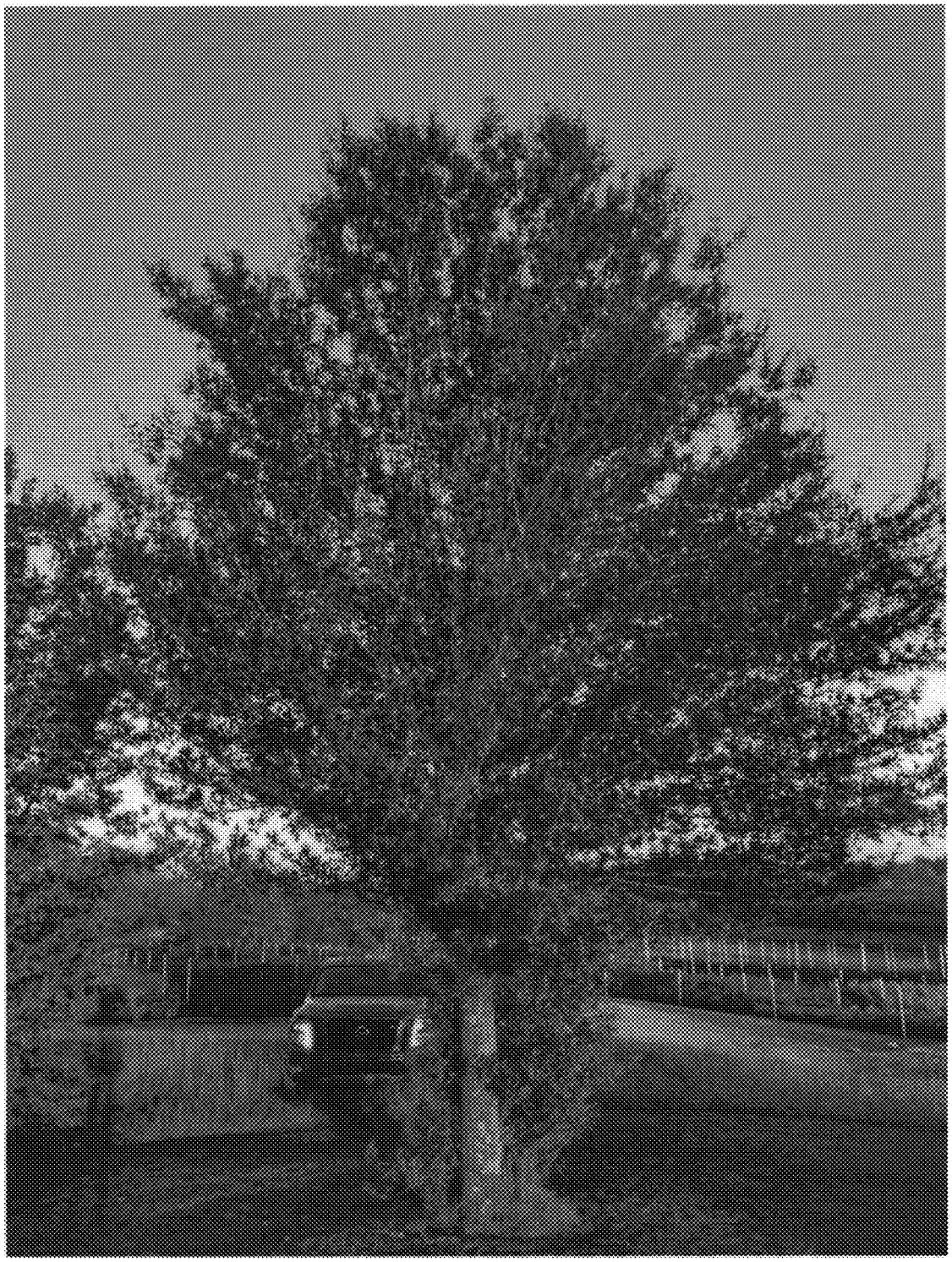
FIG. 1 illustrates, as nearly true as it is reasonably possible to make the same in color photographs of this type, the original 'TGO-GAL' tree at approximately 19 years of age, during summer in Warren County, Tenn.
Figure 2:
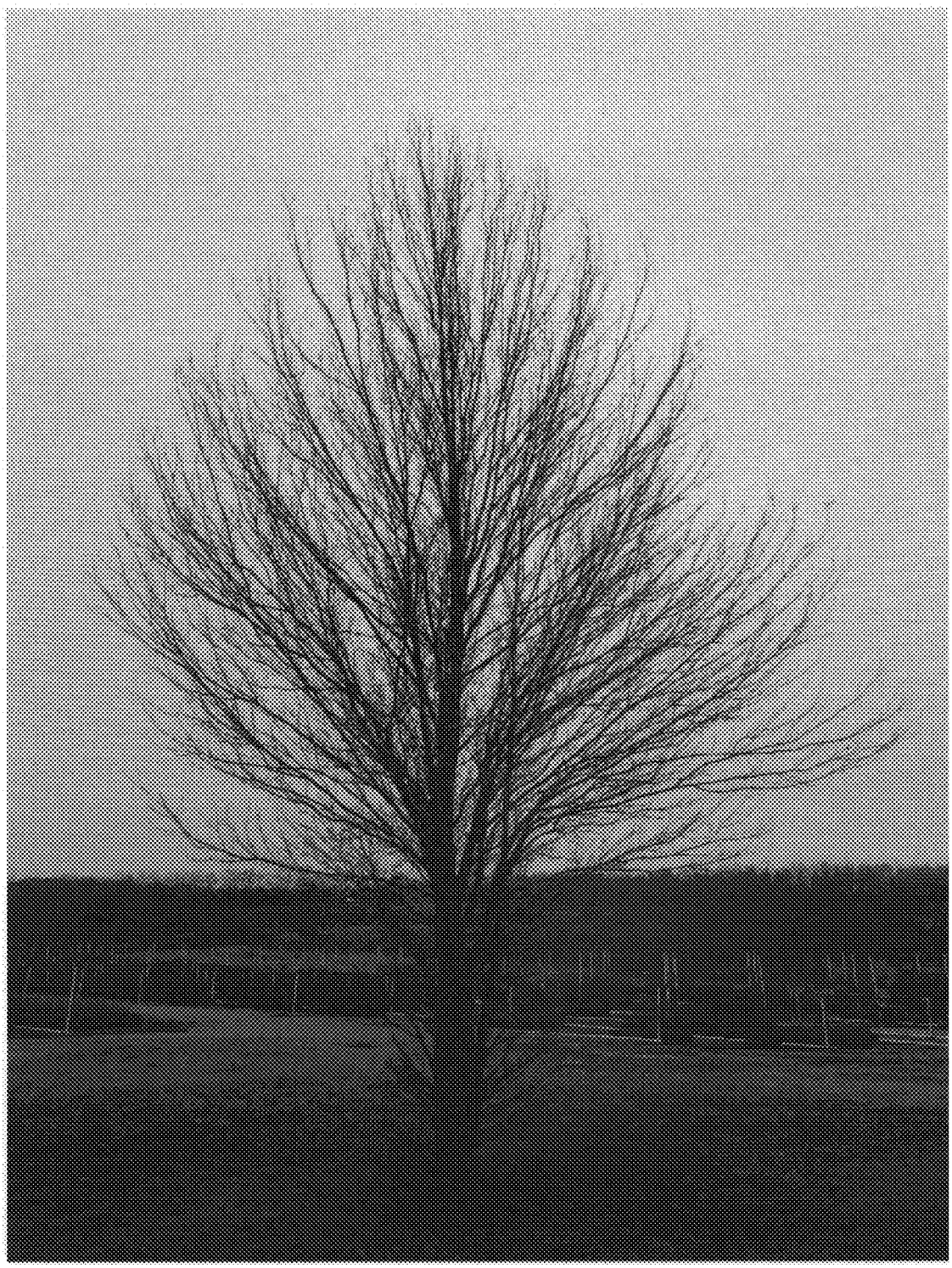
FIG. 2 illustrates, as nearly true as it is reasonably possible to make the same in color photographs of this type, the original 'TGO-GAL' tree at approximately 18 years of age, during winter in Warren County, Tenn.
Figure 3:
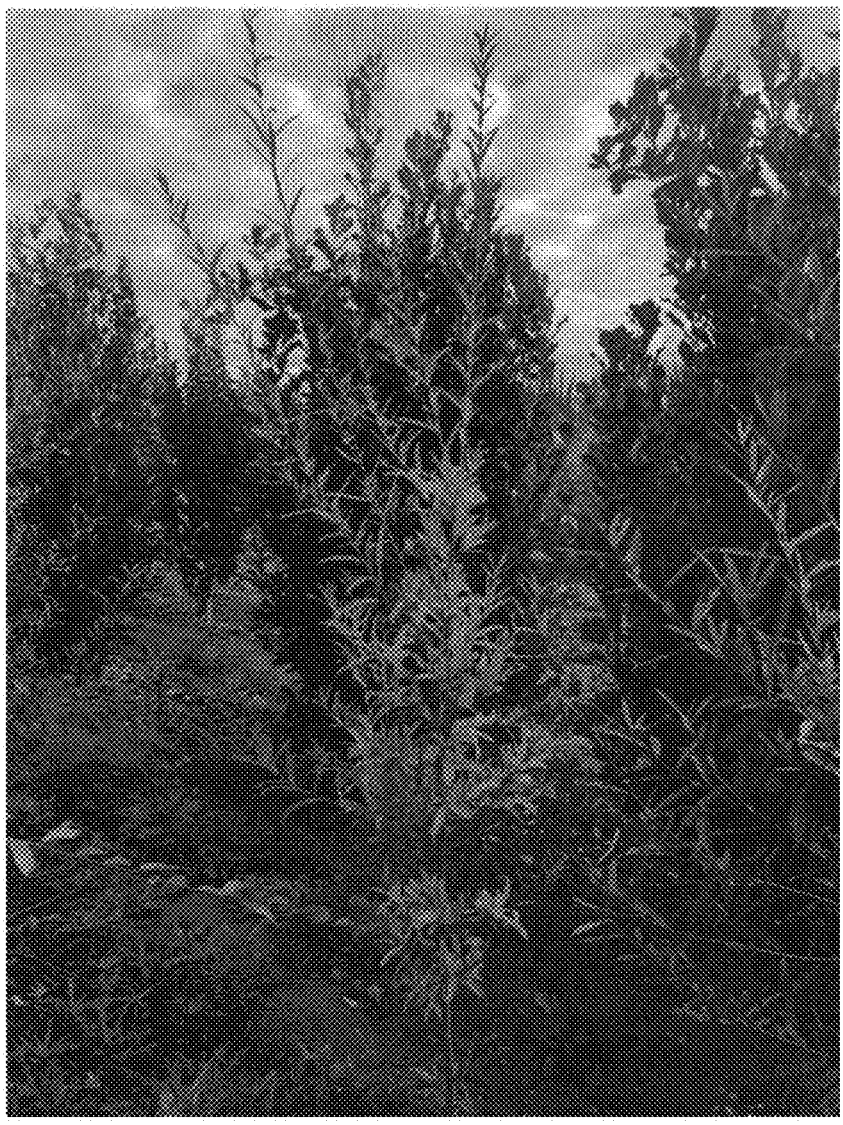
FIG. 3 illustrates, as nearly true as it is reasonably possible to make the same in color photographs of this type, the autumn foliage color of 'TGO-GAL'.

The following is a detailed botanical description of a new and distinct *Quercus phellos* plant cultivar known as 'TGO-GAL'. Plant observations were made on a 20 year-old mature tree growing in Warren County, Tenn. The observed tree was grown in full exposure to natural sunlight, maintained without the use of supplemental fertilizer or irrigation. No pest or pathogen countermeasures employed. Observation data was recorded in October of 2019.

Those skilled in the art will appreciate that certain characteristics will vary with older or, conversely, younger plants. 'TGO-GAL' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1986 edition except where common terms of color are used.

A botanical description of 'TGO-GAL' and comparisons with the parent and most similar commercial cultivar are provided below.

General plant description:

*Plant habit.*—Monoecious deciduous tree with an upright ascending, freely branching growth habit.

*Tree crown profile.*—Oval to pyramidal.

*Dimensions.*—The original tree is now approximately 11.25 meters tall and 8.25 meters wide.

*Environmental tolerances.*—Hardy in US Hardiness Zones 5 through 9; prefers moist, loamy soils and full sun exposure but will tolerate dryer conditions and light shade; drought and heat tolerant once established.

*Pest and disease susceptibility or resistance.*—Plants have not been observed to be susceptible or resistant to pathogens and pests common to *Quercus phellos*.

*Propagation.*—Propagation is accomplished using softwood stem cuttings and grafting.

*Crop time.*—Approximately two growing seasons are needed to produce an 45 to 60 cm tall fully rooted cutting ready for transplant into larger nursery containers or directly into the ground for field production.

Root system:

*Description.*—A network of fibrous, non-fleshy roots.

*Rooting habit.*—Freely branching, moderately dense, and evenly distributed throughout the soil profile.

Stems:

*Branching habit.*—A dominant, near-vertical central main stem, occasionally branched, gives rise to an abundance of lateral branches, themselves freely branching. Main stem; central leader — Quantity — One; occasionally branching. Attitude — Erect; near vertical. Aspect — Generally rounded. Diameter — 33 cm, at the base of the trunk. Color, juvenile — Greyed-green, nearest to a mixture of RHS 197B, 197C, and 197D; irregularly blotched and banded with greyed-green, nearest to RHS 196B. Moderately suffused with a mixture of green, RHS 144A, and yellow-green, RHS 146D; suffusion becomes less pronounced as the wood ages. Color, oldest wood — Brown, nearest to a mixture of RHS 200A, 200B, 200C and 200D; fissures are greyed-orange, nearest to in between RHS 177A and 177B. Texture — Smooth and glabrous and becoming progressively fissured and furrowed with age, at and towards the base or trunk of the tree. Strength — Very strong. Lateral branches — Branch angle to main axis — In between 30 and 40 degrees. Aspect — Circular; somewhat angular. Diameter — 25 mm at the base. Color, juvenile — Nearest to a mixture of greyed-orange, RHS 165A, and yellow-green, in between RHS 152A and 152B. Color, mature — Greyed-green, nearest to a mixture of RHS 197B, 197C, and 197D; irregularly blotched and banded with greyed-green, nearest to RHS 196B. Moderately suffused with a mixture of green, RHS 144A, and yellow-green, RHS 146D. Texture — Smooth, glabrous; lenticels sparsely covering immature branches. Lenticels are elliptical; approximately 1.0 mm long and 0.75 mm wide; color is greyed-brown, RHS 199D. Stem strength — Strong.

Foliage:

*Arrangement.*—Alternate.

*Attachment.*—Petiolate.

*Division.*—Simple.

*Shape.*—Elliptic.

*Length.*—88 mm.

*Width.*—25 mm.

*Apex.*—Acute to acuminate.

*Base.*—Cuneate to obtuse.

*Margin.*—Entire and moderately to heavily undulated.

*Aspect.*—Flat to longitudinally concave; occasionally with a slight axial twist.

*Texture and pubescence, adaxial surface.*—Lightly rugose, glabrous, and glossy.

*Texture and pubescence, abaxial surface.*—Rugose, glabrous and matte.

*Color, spring.*—Juvenile foliage, adaxial surface — Nearest to in between orange-red and red, RHS 33A, 34A, and 40A; becoming progressively suffused with yellow-green, RHS 146A, as leaves mature. Juvenile foliage, abaxial surface — Orange-red, nearest to RHS 34B, and becoming progressively suffused with yellow-green, nearest to in between RHS 146B and 146C, as leaves mature. Mature foliage, adaxial surface — Yellow-green, RHS 146A. Mature foliage, abaxial surface — Yellow-green, nearest to in between RHS 146B and 146C.

*Color, summer.*—Juvenile foliage, adaxial surface — Yellow-green, RHS 146A. Juvenile foliage, abaxial surface — Yellow-green, nearest to in between RHS 146B and 146C. Mature foliage, adaxial surface — Yellow-green, RHS 146A. Mature foliage, abaxial surface — Yellow-green, nearest to in between RHS 146B and 146C.

*Color, autumn.*—Juvenile foliage, adaxial surface — Nearest to in between orange-red and red; RHS 33A, 34A and 40A. Juvenile foliage, abaxial surface — Orange-red, nearest to RHS 34B. Mature foliage, adaxial surface — Yellow-green, RHS 146A, and progressively fading to a lighter shade of yellow-green, nearest to in between RHS 151C and 154A, as leaves near abscission and ultimately becoming yellow, nearest to in between RHS 9A and 13B, prior to abscission. Mature foliage, abaxial surface — Yellow-green, nearest to in between RHS 146B and 146C, and progressively fading to a lighter shade of yellow-green, nearest to in between RHS 151C and 154A, as leaves near abscission and ultimately becoming yellow, nearest to in between RHS 9A and 13B, prior to abscission.

*Venation.*—Pattern — Pinnate. Vein color, adaxial surface — Greyed-yellow, nearest to RHS 162D, and moderately suffused with yellow-green, RHS 146D.

Vein color, abaxial surface — Greyed-yellow, nearest to RHS 162D, and lightly suffused with yellow-green, RHS 146D.

*Petiole.*—Length — 5.0 mm. Diameter — 1.5 mm. Color, adaxial surface — Greyed-yellow, nearest to RHS 162D, and moderately suffused with yellow-green, RHS 146D. Color, abaxial surface — Greyed-yellow, nearest to RHS 162D, and moderately suffused with a mixture of yellow-green, RHS 146D, and greyed-orange, RHS 164B. Texture, adaxial and abaxial surfaces — Smooth; glabrous.

*Stipules.*—Absent.

Inflorescence: To date, no flowering has been observed on the mother plant or any progeny therefrom.

Flower bud: To date, no flowering has been observed on the mother plant or any progeny therefrom.

Flower: To date, no flowering has been observed on the mother plant or any progeny therefrom.

Reproductive organs: To date, no flowering has been observed on the mother plant or any progeny therefrom.

Fruit and seed: To date, no fruiting has been observed on the mother plant or any progeny therefrom.

Comparison with the presumed parent plant: Plants of the new cultivar 'TGO-GAL' differ from the parent, an unnamed *Quercus phellos* tree (not patented), by the characteristics described in Table 1. The pollen parent is presumed to also be an unnamed *Quercus phellos* tree (not patented), and therefore no additional comparison to the pollen parent is disclosed.

TABLE 1

| Characteristic | 'TGO-GAL' | The parent |
|---|---|---|
| Tree crown profile. | Oval to pyramidal. | Rounded to oval. |
| Branch crotch angle, relative to the main axis. | Ranging from 35 to 45 degrees; crotch angles remain consistent with age. | Ranging from 35 degrees, distally, to 130 degrees, proximally. |

TABLE 1-continued

| Characteristic | 'TGO-GAL' | The parent |
|---|---|---|
| General springtime coloration of the juvenile foliage. | Red. | Green. |
| General autumn coloration of the foliage. | Red juvenile foliage and yellow mature foliage. | Yellow juvenile foliage and mature foliage. |

Comparison with the most similar *Quercus phellos* cultivar known to the inventor: Plants of the new cultivar 'TGO-GAL' are most similar to the commercial cultivar, *Quercus phellos* 'RT3' (U.S. Pat. No. 16,444). A comparison of 'TGO-GAL with *Quercus phellos* 'RT3' is described in Table 2.

TABLE 2

| Characteristic | 'TGO-GAL' | 'RT3' |
|---|---|---|
| Growth habit; height to width ratio. | Approximately 1.35:1, height to width. | Approximately 2.0:1, height to width. |
| Tree crown profile. | Oval to pyramidal. | Rounded to oval. |
| Branch crotch angle, relative to the main axis. | Ranging from 35 to 45 degrees; crotch angles remain consistent with age. | New lateral branches emerge at an angle of 20 to 30 degrees and mature to 30 to 40 degrees. |
| General springtime coloration of the juvenile foliage. | Red. | Green. |
| General autumn coloration of the juvenile foliage. | Red. | Yellow. |
| Fruiting. | Non-fruit bearing. | Fruit bearing. |

That which is claimed is:

1. A new and distinct variety of *Quercus phellos* tree named 'TGO-GAL', substantially as described and illustrated herein.

* * * * *